United States Patent [19]

Bille et al.

[11] Patent Number: 4,848,340

[45] Date of Patent: Jul. 18, 1989

[54] EYETRACKER AND METHOD OF USE

[75] Inventors: Josef F. Bille, Solana Beach; Stuart I. Brown, La Jolla, both of Calif.

[73] Assignee: Intelligent Surgical Lasers, San Diego, Calif.

[21] Appl. No.: 154,859

[22] Filed: Feb. 10, 1988

[51] Int. Cl.$^4$ ............................................. A61B 17/36
[52] U.S. Cl. ................................. 128/303.1; 351/210; 128/745
[58] Field of Search ............... 351/200, 201, 202, 203, 351/208, 209, 210, 236; 128/303.1, 303.13, 303.14, 395

[56] References Cited

U.S. PATENT DOCUMENTS

| | | | |
|---|---|---|---|
| 4,053,845 | 10/1977 | Gould | 330/4.3 |
| 4,161,436 | 7/1979 | Gould | 204/157.1 R |
| 4,287,410 | 9/1981 | Crane et al. | 351/210 |
| 4,443,075 | 4/1984 | Crane | 351/209 |
| 4,503,854 | 3/1985 | Jako | 128/303.1 |
| 4,517,980 | 5/1985 | Tagnon | 128/395 |
| 4,561,436 | 12/1985 | Munnerlyn | 128/303.1 |
| 4,579,430 | 4/1986 | Bille | 351/206 |
| 4,598,311 | 7/1986 | Bellina | 358/93 |
| 4,601,288 | 7/1986 | Myers | 128/303.1 |
| 4,665,913 | 5/1987 | L'Esperance, Jr. | 128/303.1 |
| 4,669,466 | 6/1987 | L'Esperance | 128/303.1 |
| 4,702,575 | 10/1987 | Breglia | 351/210 |
| 4,704,583 | 11/1987 | Gould | 330/4.3 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,784,135 | 11/1988 | Blum et al. | 128/303.1 |

OTHER PUBLICATIONS

"FM-Laser Operation of the ND:YAG Laser," by Kuizenga et al., IEEE Journal of Quantum Electronics, Nov. 1970.

"Laser Interactions with the Cornea", by Krauss et al, Survey of Ophthalmology, Jul.-Aug. 1986.

"Configuring an Electrostatic Membrane Mirror by Least-Squares Fitting with Analytically derived Influents Functions," Claflin et al., J. Opt. Am. A., Nov. 1986.

"Defects in the Optical Synthesis," published and date unknown.

Primary Examiner—Francis Jaworski
Assistant Examiner—George Manuel
Attorney, Agent, or Firm—Nydegger & Harshman

[57] ABSTRACT

An eyetracker for moving the path of a laser beam in response to patient eye movement comprises a visual light source on which the patient can fixate to bring the visual axis of the eye into a reference alignment with the optical axis of the light source. A laser source, having its beam coaxially aligned with the optical axis of the light source, cuts a mark onto the cornea of the eye when the eye is in the reference alignment. An infrared optical system monitors movement of the mark to generate an error signal which is proportional to any movement of the mark out of the reference alignment. Means are also provided by the eyetracker to move the path of the laser beam back into the reference alignment to reduce the error signal to a null.

25 Claims, 4 Drawing Sheets

EYETRACKER AND METHOD OF USE

BACKGROUND OF THE INVENTION

This invention relates to guidance systems for laser surgery. More specifically, the present invention relates to a control system which is able to precisely maintain the proper position of a laser beam during surgery. This invention is particularly, but not exclusively useful for controlling a laser surgical device during ocular surgery without immobilizing the eye.

DISCUSSION OF THE PRIOR ART

Medical surgical procedures using laser beams to alter tissue in the target area have been practiced for many years with great success. Fortunately, as our knowledge of lasers is increased, there is a concomitant recognition of new ways in which lasers can be effectively employed. Ophthalmic surgery is one field of use where new uses for laser surgery have been efficaciously applied.

A real problem with ophthalmic or ocular surgery, however, is the fact that the eye is so easily moved. Additionally, of course, the sensitivity of this very delicate organ creates a whole set of unique concerns. Thus, there is a widely recognized need to be extremely precise with any procedure which alters tissue of the eye. It happens that the more precise the surgical instrument can be in its operation, the more there is a desire to benefit from that precision by having accurate control over the instrument in its relationship with the eye.

In the past, various attempts have been made to fixedly hold the eye during ocular surgery. An example of a device intended for this purpose is found in U.S. Pat. No. 4,665,913 to L'Esperance Jr. wherein an eye retaining fixture is disclosed. Specifically, a device of this type is suctionfitted onto the eye to establish external means by which the eye can be held. As might be expected, the use of such a device can be very painful for the patient and the efficacy of such a device can be questioned.

Unlike the devices of the prior art which require immoblization of the eye in order to achieve their precision, the present invention achieves the required operative precision while allowing the eye some degree of movement. Specifically, the present invention recognizes that precise ophthalmic surgical procedures can be accomplished without immobilizing the eye. This is possible because, unlike the prior art devices, the present invention further recognizes that an ophthalmic surgery device can be programmed to track the eye by monitoring references which are marked on the eye in a known relationship with the visual axis of the eye.

In light of the above, it is an object of the present invention to provide an eyetracker with will keep an ophthalmic surgery device in a preprogrammed relationship with the visual axis of the eye during surgery. Another object of the present invention is to provide an eyetracker which allows the accomplishment of ophthalmic surgical procedures without immobilizing the eye. Still another object of the present invention is to provide a device which is useful for identifying either the visual axis or the symmetrical axis of the eye. Yet another object of the present invention is to provide a reference grid on the cornea of the eye which has a known relationship with the visual axis of the eye and which precisely identifies the areas of the cornea on which surgical procedures are to be performed. A further object of the present invention is to provide an eyetracker for use with ophthalmic laser surgical instruments which is easy to operate, relatively easy to manufacture and which is cost effective.

SUMMARY OF THE INVENTION

A preferred embodiment of the novel eyetracker comprises a visual light source on which a patient can fixate to coaxially align the visual axis of the patient's eye with a segment of the axis of the visual light beam. A laser source also coaxially aims its beam along this axis segment of the visual light beam. Thus, when the patient's eye is fixated, a reference alignment is established between the eye's visual axis and the laser beam since the eye's visual axis and the laser beam are both coaxially aligned on the same axis segment. While the patient's eye is initially in reference alignment, the laser source is activated to mark a grid on the cornea of the patient's eye which fixes a known relationship between the grid and the eye's visual axis.

A source of diffused infrared light is provided to illuminate the grid marked cornea. Reflections therefrom are optically directed to a sensor where movements of the grid out of its reference alignment are detected. At the sensor, variations in the intensity of the reflected infrared light are used to generate signals which are representative of any grid movement. These signals are then transmitted by electronic means from the sensor to a comparator. In the comparator, each grid movement signal is compared with a reference signal which is representative of the grid position when in reference alignment. An error signal, proportional to the difference between the "grid in reference alignment" signal and the "grid movement" signal, is generated and transmitted to a guidance system which steers the laser beam in a manner that reduces the error signal to a null. While maintaining the error signal at a null, the laser beam is steered to make controlled external or internal ablations of the cornea in accordance with a predetermined computerized program.

In addition to the use of diffused infrared light for monitoring grid movement to establish a closed loop feedback control for the laser guidance system, the source of diffused infrared light may also be used to help identify the eye's axis of symmetry. For this latter purpose, the sensor is focused on the plane of the iris rather than on the cornea. When focused on the plane of the iris, the sensor is focused along a plurality of lines to detect the intensity of the light that is reflected from the sclera, the iris and the pupil. The sensor then transmits this information to a computer which uses it to precisely determine the exact relationship between sclera, iris and pupil. Also, a beam of collimated infrared light from a laser diode is focused onto the cornea. In alternation with its focus on the iris plane, the sensor is focused on the cornea to scan the cornea and detect specular reflections from the beam of collimated infrared light. Due to the shape of the cornea, the specular reflection of greatest intensity will come from the apex of the cornea. Since the sensor is preferably a line diode, the apex of the cornea is identified when the most intense specular reflection falls on the center of the line diode. This information is also sent to the comparator where information from the iris plane concerning the relationship of the sclera, iris and pupil, and information from the corneal plane concerning the apex of the cornea are used together to determine the eye's axis of symmetry.

With the information obtained as discussed above, surgical laser operations on the cornea can be accomplished using the reference alignment without immobilizing the eye. This is accomplished whether the reference alignment is made directly on the visual axis of the eye or on the visual axis as empirically determined by its relationship with the eye's axis of symmetry.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
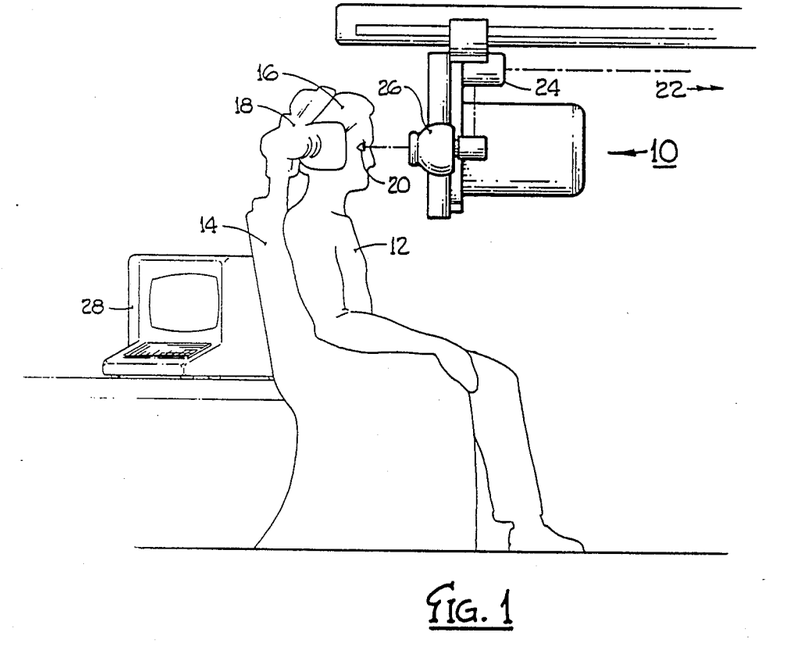
FIG. 1 is a side elevation view of surgical equipment comprising the present invention operatively positioned for surgery on a patient's eye.

Referring initially to FIG. 1, it is to be appreciated that the eyetracker of the present invention is a component of a surgical laser device generally designated 10. As shown in FIG. 1, surgical laser device 10 with its component eyetracker is operatively positioned for surgical procedure on patient 12. Although patient 12 shown sitting in a chair 14 for purposes of ophthalmic or ocular surgery, it is to be understood that patient 12 may be placed in a reclining position on an operating table (not shown) without compromising the effectiveness of the present invention.

The patient 12, while sitting in chair 14, is placed with his/her head 16 positioned within restraint 18 for purposes of restricting movement of his/her head during surgical operations. In accordance with the present invention, the eye 20 of patient 12 need not be immobilized during surgery. Instead, the present invention is intended to compensate for modest movements of eye 20.

Figure 2:
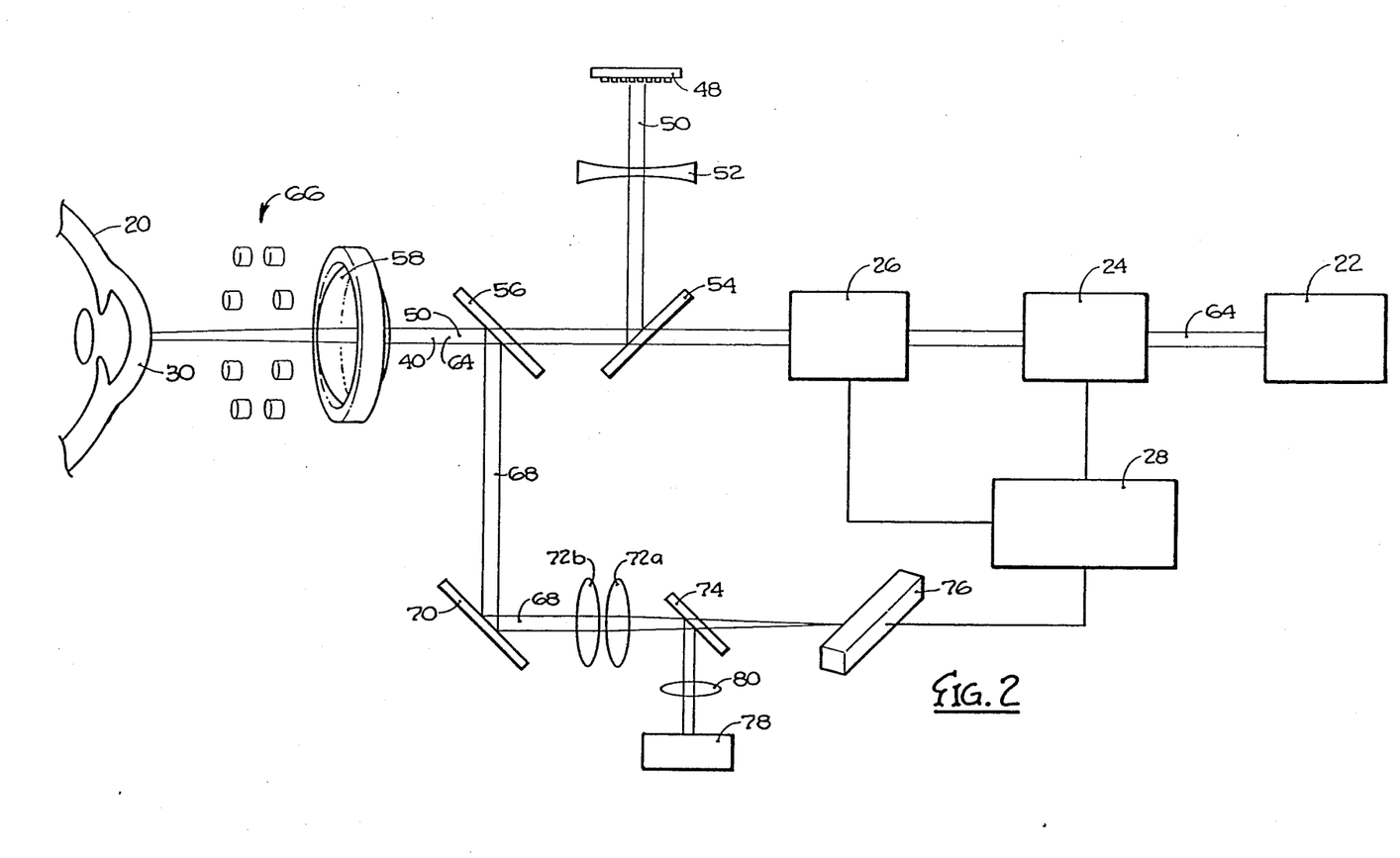
FIG. 2 is a schematic view of the eyetracker and its associated optical elements shown in relationship with a cross-sectional view of a portion of an eye.

It is to be understood that the present invention is preferably intended for use with a laser guidance system of the type disclosed in our co-pending application for an invention entitled "3 Dimensional Laser Beam Guidance System" which was filed on Jan. 27, 1988 and which is incorporated herein by reference. The major components of this guidance system are shown in FIG. 2 in cooperation with elements of the present invention and are shown to generally comprise a fine tuner 24, a focusing element 26 and a laser source 22 of a type disclosed in our co-pending application entitled "Multi- wavelength Laser Source" which was filed on Feb. 2, 1988 and which is incorporated herein by reference. A comparator (computer) 28 is shown electrically connected to provide programmable input for fine tuner 24 and focusing element 26 of the guidance system.

Figure 3:
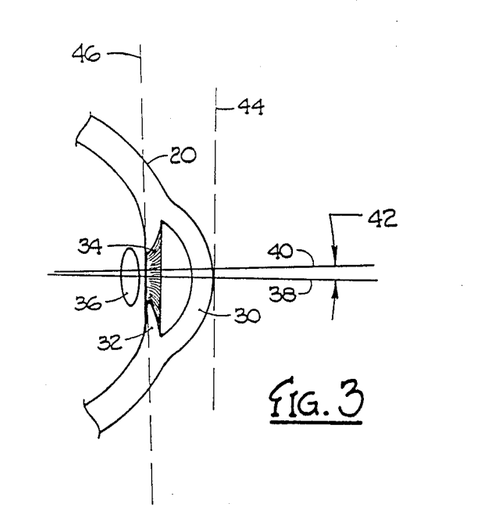
FIG. 3 is a cross-sectional view of a portion of an eye.

Referring for the moment to FIG. 3, a brief description of eye 20 and certain of its geometric properties will be helpful. Specifically, in FIG. 3 it will be seen that a cross-section of eye 20 reveals a cornea 30 which is set apart from the iris 32 of eye 20. It will also be appreciated that iris 32 establishes pupil 34 of eye 20 and that a lens 36 is functionally positioned relative to the iris and behind the pupil, substantially as shown. A greater detailed description of the human eye 20 need not be provided for an adequate description of the functioning of the present invention. However, some very important concepts with regard to the alignment of eye 20 are important insofar as the present invention is concerned.

It is well known that the human eye can be discussed with regard to two separate axes. First, there is the axis of symmetry 38. Essentially, as the name implies, the axis of symmetry 38 is that axis about which a rotation of a section of the eye will generate a three dimensional model of the complete eye. It happens, however, that the visual functioning of the eye does not occur along the axis of symmetry 38. Instead, visual acuity occurs along a visual axis 40. As indicated in FIG. 3, there is a slight off-set 42 between the axis of symmetry 38 and the visual axis 40. Although the magnitude of this off-set will vary slightly from individual to individual, it can be empirically determined and is generally around five degrees. It is also helpful for an understanding of the present invention to define the corneal plane 44 as that plane which is tangential to the cornea 30 at the point where the axis of symmetry 38 is normal to cornea 30. Also, it is helpful to define the iris plane 46 as that plane which generally passes across the pupil 34 between the diametrical extensions of iris 32.

Referring back to FIG. 2, it will be seen that the eyetracker of the present invention includes a source of visible light 48. Preferably, source 48 is a quadratic array of light emitting diodes which radiate blue-green light. Light beam 50, which radiates from visible light source 48, passes through a negative lens 52 and is reflected by turning mirror 54 toward a selectively reflective mirror 56. After passing through mirror 56, beam 50 of visible light passes through objective lens 58 and is incident upon cornea 30 of eye 20. Preferably, and for reasons to be more clearly apparent after subsequent discussion, selectively reflective mirror 56 is transparent for visible light and for all wavelengths used for the cutting laser beam for laser source 22. On the other hand, selectively reflective mirror 56 should be reflective for infrared components of light and, more specifically, mirror 56 should be reflective of infrared light having wavelengths which are radiated by diode array 66.

It will be recalled that visual axis 40 is the most important reference insofar as vision is concerned. Therefore, in ocular surgery, some operative reference to visual axis 40 needs to be established. This is done, in accordance with the present invention, by directing visible light from source 48 toward eye 20 to establish a spot of light upon which the patient 12 can fixate. Accordingly, if patient 12 fixates on the beam 50 of light coming from source 48, the visual axis 40 of eye 20 will be coaxially aligned with beam 50. This coaxial alignment is extremely important insofar as the present invention is concerned since, as inferenced above, in ophthalmic or ocular surgery it is desirable that corneal surgical procedures be accomplished with reference to the visual axis 40.

With visual axis 40 of eye 20 coaxially aligned along a portion of beam 50 of visible light, a reference grid 60 is marked on the cornea 30 of eye 20. This marking of grid 60 is accomplished by laser beam 64 which originates at source 22. Specifically, laser beam 64 is coaxially aligned within device 10 along that portion of beam 50 which is directed by turning mirror 54 toward eye 20. Thus, when patient 12 fixates on beam 50, laser beam 64 is coaxially aligned with the visual axis 40 of eye 12. This caged coaxial alignment between visual axis 40 and laser beam 64 is referred to herein as the reference alignment and is used by the eyetracker of the present invention as a base from which subsequent movement of laser beam 64 is monitored.

Figure 4:
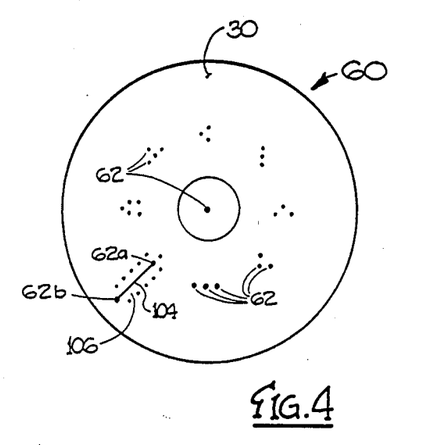
FIG. 4 is a front plan view of an eye marked with a grid.

Optically, device 10 uses movement of grid 60 to control movement of laser beam 64. Therefore, grid 60 must be marked when visual axis 40 and laser beam 64 are in reference alignment. Specifically, as patient 12 fixates on beam 50 from light source 48, laser source 22 is activated and steered by proper programmed input to fine tuner 24 in a manner which will establish a grid or template of small incisions on cornea 30 of eye 20. Momentarily referring to FIG. 4, a grid generally designated 60, as envisioned by the present invention, is shown marked on cornea 30 of eye 20. From FIG. 4, it will be appreciated that a series of spots 62 are cut into cornea 30 in any manner desired by the operator for subsequent procedures. As shown in FIG. 4, groups of spots 62 may be arranged in a coded fashion. Such coding can be subsequently used at comparator 28 to further identify the orientation of eye 20. Preferably, spots 62 are small incisions created in cornea 30 by the cutting laser 64 from laser source 22. Further, it is preferable that spots 62 be approximately ten microns in depth and approximately ten microns in diameter. It has been found, in accordance with the present invention, that these small spots when cut into cornea 30, provide a sufficient optical reference for further operation of the eyetracker.

Referring back to FIG. 2, it will be seen that a monitoring system is provided to effectively track movement of eye 20. For this purpose, an annular array of diodes 66 is positioned in device 10 between eye 20 and objective 58 to radiate diffused infrared light onto cornea 30 of eye 20. This light will be reflected from cornea 30 with information concerning the spots 62 which have been cut into cornea 30 to establish grid 60. This reflected light passes through objective 58 and is incident on selectively reflective mirror 56 where it is further reflected along a path 68 toward galvanometric mirror 70. Although selectively reflective mirror 56 can be established to reflect various wavelengths of light, this reflectivity must be compatible with the light emitted from diode array 66. Therefore, preferably, mirror 56 is reflective of light having wavelengths approximately 940 nanometers. Such wavelength would be typical for an infrared source such as intended for diode array 66. On the other hand, it will be understood that selectively reflective mirror 56 must be transparent for light coming from source 48 and source 22.

The infrared light reflected from cornea 30 with information regarding grid 60 is reflected by galvanometric mirror 70 where it is directed to pass through a pair of convex lenses 72a and 72b. After passing through convex lenses 72a and 72b, this infrared light is incident on 50% mirror 74 where half the light is passed toward linear diode 76. Linear diode 76 is preferably a line of individual light sensitive sensors or pixels. Thus, galvanometric mirror 70 can be continuously rotated in a well known manner to provide linear diode 76 with a scanning coverage of eye 20. Signals generated by such a device can then be used in a manner well known in the art.

FIG. 2 also shows that linear diode 76 is operatively connected with comparator 28. Through this connection, information concerning the movement of grid 60 can be transmitted to comparator 28 for comparison with a signal representative of the reference alignment. Comparator 28 then generates an error signal proportional to the difference between the actual position of grid 60 as detected by the sensor linear diode 76, and the desired position of grid 60 in its reference alignment. This error signal is used by fine tuner 24 to guide laser beam 64 in a manner which reduces the error signal to a null.

Under certain conditions, i.e. the patient is uncooperative or unable to cooperate, it may be difficult or impossible to identify visual axis 40. Therefore, it may be necessary to just identify the axis of symmetry 38 and then empirically determine visual axis 40. For this purpose, FIG. 2 also shows that an infrared light emitting diode 78 can be provided as a source of infrared light. Infrared light from diode 78 passes through a collimating lens 80 before being incident on 50% mirror 74. It will be understood that upon reflection from mirror 74 collimated infrared light from source 78 is directed by mirror 70 and mirror 56 and through lens 58 onto cornea 30 of eye 20. As previously indicated, galvanometric mirror 70 is moveable to scan the beam of collimated light from source 78 along scan lines on cornea 30. Reflections of light from these scan lines are detectable by linear diode 76 and information contained in the reflections can be transmitted to comparator 28 for use by device 10. Specifically, this use relates to identification of the symmetrical axis of eye 20 in a manner to be disclosed below.

Figure 5:
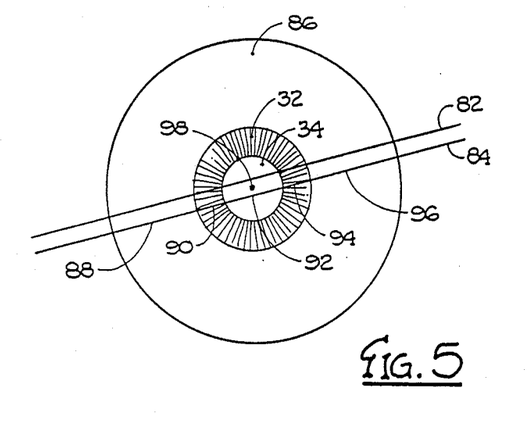
FIG. 5 is a front plan view of an eye shown with superposed representative scan lines.

It will be understood that with the movement of galvanometric mirror 70, device 10 is able to reflect collimated light from source 78 and diffused light from diode array 66 to linear diode 76 where the reflections will be sensed as line scans. Referring for the moment to FIG. 5, examples of such scan lines in iris plane 46 are shown as lines 82 and 84. Still referring to FIG. 5, it can be appreciated that a scan along line 84 will reflect light from the sclera 86, the iris 32 and the pupil 34 of eye 20. Importantly, the intensity of reflected light from these parts of eye 20 will vary according to a graph generally shown in FIG. 6. Cross-referencing FIG. 5 with FIG. 6 indicates that the intensity of reflections at point 88 on sclera 86 corresponds to comparable point 88 in FIG. 6 relative to the intensity of the reflected light. Likewise, points 90, 92, 94 and 96 respectively are shown in FIG. 6 as intensity variations along line 84.

Figure 6:
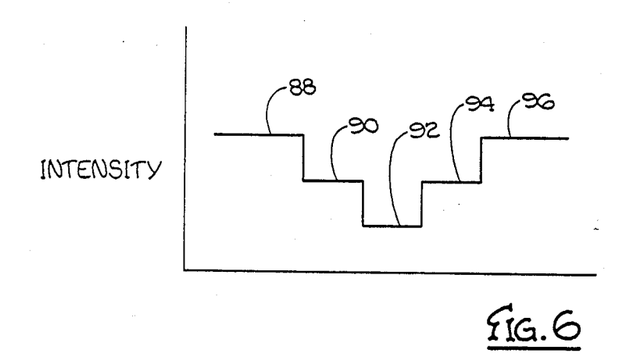
FIG. 6 is a graph of the intensity of light reflected from the iris plane of an eye along a preselected scan line.

Providing information for comparator 28 in the form of signals which are proportional to the intensities of reflected light, as generally shown in FIG. 6, allows for a profile mapping of eye 20. The precision of the profile is enhanced by taking a plurality of such measurements along a series of scan lines. Scan lines 82 and 84 are only exemplary.

Figure 7:
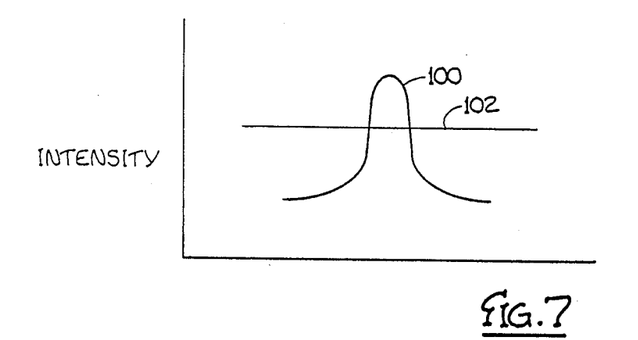
FIG. 7 is a graph of the intensity of light reflected from the cornea of an eye under prescribed conditions.

Recall that information in the collimated infrared light from light emitting diode 78 which is reflected from cornea 30 is also available for use by comparator 28. It happens that this light is specularly reflected from the cornea and that its intensity, sensed by linear diode 76, is dependent on whether the reflected light is focused. Therefore, since the cornea is not perfectly spherical, apex 98 of cornea 30 will reflect more intense light than other spots on cornea 30 when objective 58 is focused on corneal plane 44. The result, when mirror 70 moves to scan cornea 30, is an intensity variation of light which is reflected to linear diode 76 that generally follows the graph 100 depicted in FIG. 7. Making linear diode 76 responsive to the intensity whenever it passes some threshold value 102 allows a rather precise identification of apex 98. It follows that by alternating the focus between iris plane 46 and the corneal plane 44 in which apex 98 lies, information concerning the location of apex 98 relative to iris 32 and pupil 34 can be obtained. From this, the axis of symmetry 38 of eye 20 is determined.

Based upon an empirical determination of the off-set 42 between the symmetrical axis 38 of eye 20 and the visual axis 40 of eye 20, it will be possible to control laser beam 64 with reference to either axis. This is so since the reference alignment can be related through the visual axis 40 to symmetrical axis 38. Thus, when referencing symmetrical axis 38, movement of eye 20 can be detected by linear diode 76 by monitoring the specular reflection from the apex 98 of cornea 30.

OPERATION

Figure 8:
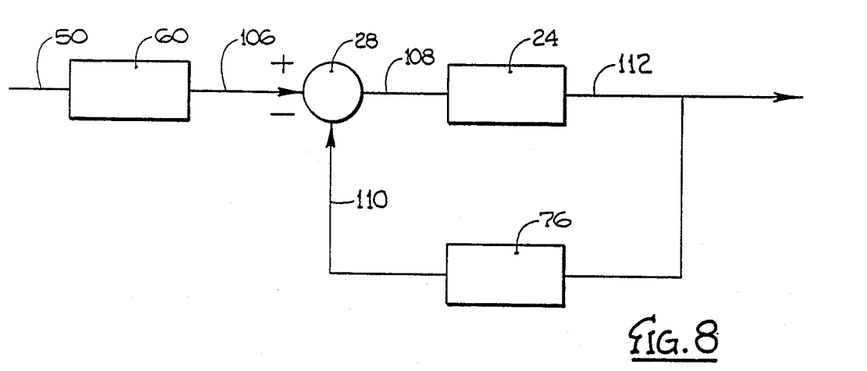
FIG. 8 is a functional block diagram of a closed-loop feedback system as incorporated into the electronic circuitry of the eyetracker.

The actual operation of the eyetracker for surgical laser device 10 will be best appreciated by reference to the functional block diagram of a closed loop control system shown in FIG. 8. Specifically, when conforming the elements of device 10 with the block diagram of FIG. 8, it will be appreciated that a reference input 106 is provided to comparator 28 which represents the reference alignment. In accordance with previous disclosure, the reference alignment contains information pertaining to the actual location of beam 50 in an established relationship with laser beam 64.

Briefly, the reference alignment is established by first having patient 12 fixate on beam 50. This fixation coaxially aligns visual axis 40 of eye 20 with the axis of beam 50. Since device 10 is built with beam 50 and laser beam 64 in coaxial alignment, this fixation also coaxially aligns visual axis 40 with laser beam 64. This relationship is what has been referred to herein as the reference alignment. Then, with visual axis 40 in reference alignment, laser beam 64 is used to mark a grid 60 onto cornea 30 of eye 20. Thereafter, laser beam 64 is steered in a predetermined manner with reference to grid 60 to cut or alter tissue in cornea 30. If eye 20 is immobilized during surgery, nothing more would need to be done. In accordance with the present invention, however, eye 20 need not be immobilized. Therefore, feedback control is required to maintain laser beam 64 in reference alignment.

Feedback control is provided for device 10 by transmitting an error or actuating signal 108 to fine tuner 24. According to feedback control theory, error signal 108 is proportional to the difference between reference input 106 and feedback signal 110. The dynamic unit, i.e. fine tuner 24, provides an output 112 which reorients laser beam 64 into a reference alignment according to error signal 108 for further surgical operation. This output 112 from fine tuner 24 is also provided as feedback which is used to generate feedback signal 110. More specifically, linear diode 76 is an optical sensor which monitors grid 60, and hence, the actual alignment of visual axis 40. Variations of this actual alignment from the reference alignment are manifested as error signal 108 from comparator 28. Stated differently, in accordance with the present invention, reflected light from the cornea 30 of eye 20 containing information regarding the position of grid 60 is transmitted by linear diode 76 as feedback signal 110 to comparator 28. Feedback signal 110 then is representative of the actual position of visual axis 40. As indicated above, comparator 28 compares the reference alignment of visual axis 40 with the actual alignment of visual axis 40 to generate error signal 108. In response to error signal 108, comparator 28 actuates fine tuner 24 in a manner which will keep laser beam 64 in its preprogrammed operation.

In a slightly different operation, the symmetrical axis 38, rather than visual axis 40, is identified by device 10. Since surgical operations must be referenced to visual axis 40, the empirically determined relationship between symmetrical axis 38 and visual axis 40 is used to make the necessary transfer. Importantly, unlike the previously described operation, when the symmetrical axis 38 is used there is no need to mark eye 20 and patient 12 need not necessarily cooperate.

To establish the symmetrical axis, a source of diffused infrared light, e.g. diode array 66, is used to provide reflected light from iris plane 46. Also, a source of collimated infrared light, e.g. light emitting diode 78, is used to provide specular reflections from corneal plane 44. Linear diode 76 is then programmed to alternatingly focus between the iris plane 46 and corneal plane 44. Signals from this operation are transmitted to comparator 28 where the reflections from sclera, iris and pupil in the iris plane 46 are compared with reflections from apex 98 of cornea 30 in the corneal plane 44 to establish a spatial relationship therebetween. With this spatial relationship, comparator 28 can establish the location of axis of symmetry 38. With this information, comparator 28 can then generate an error signal 108 which is used by device 10 in a manner previously disclosed.

Laser beam 64 is maintained in reference alignment and moved in a manner which accomplishes the desired surgical operation regardless whether visual axis 40 is directly determined, or indirectly determined through its relationship with symmetrical axis 38. For example, in FIG. 4 it can be seen that once grid 60 is established, laser beam 64 can be oriented on a particular spot 62 from which further operations can be accomplished. Specifically, spots 62a and 62b may be placed upon cornea 30 to establish a line 104 therebetween. It is within the contemplation of the present invention that, subsequently, a series of spots 106 can be established on cornea 30 in a manner similar to that previously described for the placement of spot 62. This establishes a template from which an incision along line 104 can be made.

While the particular eyetracker as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An eyetracker which comprises:
   means for generating a steerable laser beam aimed toward the eye of a patient for operating thereon;
   means for locating the visual axis of said eye;
   means for sensing movement of said visual axis;
   means connecting said sensing means with said laser beam to control the steering of said laser beam in a pedetermined relationship to said visual axis.

2. An eyetracker as cited in claim 1 wherein said locating means comprises means for placing a mark on said eye.

3. An eyetracker as cited in claim 2 wherein said mark placing means using said laser beam.

4. An eyetracker as cited in claim 3 wherein said locating means further comprises:
   means for generating a fixation light beam coaxially aligned with said laser beam, said fixation light beam being alignable with the visual axis of said eye; and
   means to establish a reference alignment when said visual axis of said eye is coaxial with at least a portion of said laser beam.

5. An eyetracker as cited in claim 4 wherein said mark placing means is adapted to cut a grid of incisions into the cornea of said eye using said laser beam.

6. An eyetracker as cited in claim 5 which further comprises a fine tuner positioned in the path of said laser beam for steering said laser beam.

7. An eyetracker as cited in claim 6 wherein said monitoring means comprises:
   means for generating a source of diffused infrared light aimed at said eye;
   a sensor means for detecting variations in the infrared light reflected from said eye which are caused by grid movement; and
   means coupled to said sensor means for transmitting signals proportional to said variations to said fine tuner for controlling said beam.

8. An eyetracker as cited in claim 7 wherein said means for generating a fixation light beam radiates blue-green light.

9. An eyetracker as cited in claim 1 wherein said locating means comprises:
   means for radiating a beam of collimated infrared light toward said eye;
   means for scanning said collimated infrared beam across the cornea of said eye;
   means for detecting the specular reflection of said collimated infrared beam from the apex of said cornea to generate a first signal;
   means for generating diffused infrared light;
   means for scanning said diffused infrared light across the iris of the eye to generate a second signal;
   means for combining said first and second signals to determine the symmetrical axis of said eye;
   means for relating said symmetrical axis to the visual axis of said eye; and
   means for establishing a reference alignment when the location of said symmetrical axis indicates said visual axis is coaxial with said laser beam.

10. An eyetracker as cited in claim 9 further comprising a fine tuner positioned in the path of said laser beam for steering said beam.

11. An eyetracker as cited in claim 10 which further comprises means to alternatingly select said first and said second signals.

12. An eyetracker which comprises:
    means for generating a fixation light for locating said visual axis;
    means for making a grid on said eye in a fixed relationship to said visual axis;
    means to establish a reference alignment between said cutting beam and said grid;
    means for monitoring movement of said grid out of said reference alignment to generate an error signal proportional thereto; and
    means for reducing said error signal to a null.

13. An eyetracker as cited in claim 12 wherein said means for making a grid is adapted to cut a plurality of incisions into the cornea of said eye in a predetermined pattern.

14. An eyetracker as cited in claim 13 further comprising a fine tuner for steering said beam, said fine tuner being operatively connected with said monitoring means and responsive to said error signal.

15. An eyetracker as cited in claim 14 wherein said monitoring means comprises:
    means for generating diffused infrared light aimed at said eye;
    a sensor means for detecting variations in the infrared light reflected from said eye which are caused by grid movement; and
    means for transmitting signals proportional to said variations to said fine tuner for controlling said beam.

16. An eyetracker as cited in claim 15 wherein said means for generating a fixation light radiates blue light.

17. An eyetracker as cited in claim 16 wherein said means for generating diffused infrared light produces light with a wavelength of approximately 940 nonometers.

18. A device for directing the path of a surgical laser beam in response to movement of the eye which comprises:
    means mounted on said device for orienting the eye into a reference alignment with said path of said laser beam;
    means mounted on said device for placing a mark on the cornea of said eye while said eye is in said reference alignment;
    means mounted on said device for monitoring movement of said mark;
    means connected with said monitoring means for generating an error signal indicating movement of said mark from said reference alignment; and
    means for moving said laser beam to reduce said error signal to a null.

19. A device as cited in claim 18 wherein said orienting means is a visual light source.

20. A device as cited in claim 19 wherein said marking means uses said surgical laser beam.

21. A device as cited in claim 20 wherein said marking means is adapted to form a grid comprising a plurality of incisions in the cornea of said eye in a predetermined pattern.

22. A device as cited in claim 21 further comprising a fine tuner for steering said beam, said fine tuner being operatively connected with said monitoring means and responsive to said error signal.

23. A device as cited in claim 22 wherein said monitoring means comprises:
    means for generating diffused infrared light aimed at said eye;

a sensor means for detecting variations in the infrared light reflected from said eye which are caused by grid movement; and means coupled to said sensor means for transmitting signals proportional to said variations to said fine tuner for controlling said beam.

24. A method for directing a laser beam in response to eye movement which comprises the steps of:
 (A) Orienting said eye in a reference alignment with said laser beam;
 (B) Placing a mark on said eye while said eye is in said reference alignment;
 (C) Creating an error signal proportional to the movement of said mark relative to said reference alignment; and
 (D) Moving said laser beam to reduce said error signal to a null.

25. A method for directing a laser beam in response to eye movement which comprises the steps of:
 (A) Identifying the symmetrical axis of said eye;
 (B) Determining the relationship of the visual axis of said eye to the symmetrical axis of said eye;
 (C) Moving said laser beam into a reference alignment with said visual axis;
 (D) Creating an error signal proportional to the movement of said visual axis relative to said reference alignment; and
 (E) Moving said laser beam to reduce said error signal to a null.

* * * * *